(12) United States Patent
Tertiaux et al.

(10) Patent No.: US 9,767,250 B2
(45) Date of Patent: Sep. 19, 2017

(54) COMPUTER-IMPLEMENTED METHOD FOR DESIGNING A BIOLOGICAL MODEL

(71) Applicant: Dassault Systemes, Velizy Villacoublay (FR)

(72) Inventors: Romain Tertiaux, Saint Cloud (FR); Nicolas Drufin, Pessac (FR)

(73) Assignee: Dassault Systemes, Velizy Villacoublay (FR)

( * ) Notice: Subject to any disclaimer, the term of this patent is extended or adjusted under 35 U.S.C. 154(b) by 0 days.

(21) Appl. No.: 14/570,852

(22) Filed: Dec. 15, 2014

(65) Prior Publication Data
US 2015/0178443 A1 Jun. 25, 2015

(30) Foreign Application Priority Data

Dec. 20, 2013 (EP) .................................... 13306822

(51) Int. Cl.
*G01N 33/48* (2006.01)
*G06F 19/12* (2011.01)
*G06F 19/26* (2011.01)
*G06G 7/58* (2006.01)

(52) U.S. Cl.
CPC .............. *G06F 19/12* (2013.01); *G06F 19/26* (2013.01)

(58) Field of Classification Search
CPC .......... G06F 19/18; G06F 19/22; G06F 19/24; G06F 19/345; G06F 19/3437
See application file for complete search history.

(56) References Cited

FOREIGN PATENT DOCUMENTS

EP       2 624 144 A1    8/2013

OTHER PUBLICATIONS

Extended European Search Report for European Application No. EP 13306822.1; entitled: A Computer-Implemented Method for Designing a Biological Model, dated: May 22, 2014.
Funahashi, A. et al., "CellDesigner 3.5: A Versatile Modeling Tool for Biochemical Networks," Proceedings of the IEEE, 96(8): 1254-1265 (Aug. 1, 2008).
Hu, Z. et al., "VisANT: data-integrating visual framework for biological networks and modules," Nucleic Acids Research, 33: W352-W357 (Jul. 1, 2005).
Shannon, P. et al., "Cytoscape: A Software Environment for Integrated Models of Biomolecular Interaction Networks," Genome Research, 13(11): 2498-2504 (Nov. 1, 2003).

*Primary Examiner* — Eric S Dejong
(74) *Attorney, Agent, or Firm* — Hamilton, Brook, Smith & Reynolds, P.C.

(57) ABSTRACT

A computer-implemented method for designing a biological model provides a set of biological models, each biological model comprising a plurality of elements and interactions between elements. Next the method provides groups of elements identified as identical, each element having an associated biological model. The method moves an element from a first group to a second group in order to correct the grouping of the elements; updates both groups; and creates a combined model by combining the set of biological models according to the updated groups.

17 Claims, 23 Drawing Sheets

COMPUTER-IMPLEMENTED METHOD FOR DESIGNING A BIOLOGICAL MODEL

RELATED APPLICATION

This application claims priority under 35 U.S.C. §119 or 365 to European Application No. EP Application 13306822.1, filed Dec. 20, 2013. The entire teachings of the above application are incorporated herein by reference.

TECHNICAL FIELD OF THE INVENTION

The invention relates to the field of computers programs and systems, and more specifically to the field of merging or composing biological models. Biological models describe some biological phenomenon by representing molecules (or entities or elements) and interactions between them.

BACKGROUND OF THE INVENTION

Such systems aim to analyze models, to design models, or to simulate and understand the emergent properties of complex normal and pathological living systems in order to propose a global dynamic and predictive vision.

A merging process consists in choosing which entities from input models must be grouped in the output model.

FIGS. 1, 2 and 3 illustrate a composition of models A (FIG. 1) and B (FIG. 2) for delivering an output model AB (FIG. 3). On this example, common entities are named Mp and P0. On these figures, squares represent interactions between entities. The output model AB depends on which entities are supposed to be identified in both A and B models.

This series of choices is a non-trivial process, for various reasons (a same biological phenomenon may have different modeling, models may have been made by different people, with different naming conventions, . . . ). Many criteria can be used to help making these choices, as molecules names, annotations or graph topology.

Annotations are additional data attached to the model elements which add unstructured information to the model, mostly using a text format. For instance, annotations can be used to add references to public databases. Such databases are very commonly used in the bioinformatics field.

The database provided under the trademark Uniprot is an example of a large and widely-used protein database. Each database has its own unique identifier syntax. For instance, a protein of a model could have an annotation "uniprot: P38731". The identifier "P38731" is Uniprot-specific and refers to an object in the Uniprot database: http://www.uniprot.org/uniprot/P38731 ("Siderophore iron transporter ARN1"). As these annotations are added by a user without any consistency-check, they may contain numerous errors. Moreover, some clones or ambiguities exist in public databases. These two points explain why even with fully-annotated models, merging is not a straightforward process.

The merging process can either be manual or automated by algorithms, in which case the result may contain errors and, as a result, needs a manual curing.

SUMMARY OF THE INVENTION

The present invention allows a user to go through this merging process and allows the user to correct the proposed result.

A known advanced tool in the systems biology merging domain is the software known under the trademark SemanticSBML, which is an online tool allowing the user to select biological models either from the models database provided under the trademark BioModels repository or from the user hard drive, and to combine them. The aim of the operation is to produce a single output model.

The merging user interface is presented as a table, as represented on FIG. 4, each column representing a model. Each line represents an element of the output model. If a line is filled for only one input model, it means that an element is simply copied to the output model (for instance, ACh on the screenshot). If several columns are filled for a same line, it means that this group of input models entities will lead to a single entity or element in the output model (for instance, on the screenshot, BasalACh2 from model 1 and BasalACh2 from model 2 will be combined).

For each line, the user can choose either to keep or to reject the group using a checkbox. The application also allows the user to cancel a merging group and to create a new group from preselected elements coming from input models.

With the state of the art solution, it is not possible to change an element from a merging group to another one without implying numerous interactions from the user, corresponding to numerous steps of the implemented method. For instance, if an element A needs to be added to a pre-existing merging group {B, C, D}, the user must:
 explode the group {B, C, D},
 select A, then B, then C, then D, and
 click on the "match selected" command.

The needed number of interactions to do a simple operation is a major drawback for the usability and the productivity of the application.

An example of such an operation made with SemanticSBML is presented on FIGS. 5 to 10. On FIG. 5, the element EGF of the first model is associated with the element EGFR of the second model and element EGFR of the first model is associated with element EGF of the second model. To correct the mistake, eight clicks are needed (a click is represented by a dotted circle):
 one click to explode the first group "EGF/EGFR";
 one click to explode the second group "EGFR/EGF";
 two clicks to select EGF from each model, then one click to create a new group with them ("match selected");
 two clicks to select EGFR from each model; and
 one click to create a new group with them ("match selected").

A goal of the invention is to provide a computer-implemented method and a system to overcome the above mentioned problems, and particularly to drastically limit the number of drag-and-drop operations.

It is proposed, according to one aspect of the invention, a computer-implemented method for designing a biological model comprising the steps of:
 providing a set of biological models, each biological model comprising a plurality of elements and interactions between elements;
 providing groups of elements identified as identical, each element having an associated biological model;
 moving an element from a first group to a second group in order to correct the grouping of the elements;
 updating both groups; and
 creating a combined model by combining the set of biological models according to the updated groups.

Such a method allows to the user to simplify the merging of the biological models, and limit the number of operation necessary to correct the provided groups of elements. The present method is more productive and easy-to-use.

Such a single moving interaction, in addition to the existence of a specific "non-grouped elements" group and of available empty groups, gives the ability to the user to express the whole set of merging combinations while limiting the number of user interactions.

According to an embodiment, the step of providing groups of elements identified as identical uses annotations attached to the biological models.

The use of annotations gives identifications clues to process a list of merging suggestions.

According to an embodiment, the step of providing a set of biological models uses at least one external database.

Accessing databases allows to use access databases with an unlimited number of biological models, and as soon as they are put in these databases.

According to an embodiment, the method comprises the step of partially representing the biological models around a common element, with a common annotation, in case of acceptance of the corresponding merging suggestion.

It is then possible to visualize the portion of the combined model corresponding to the element that the user is currently processing and understand the result of a merging for the neighborhoods of the element.

According to an embodiment, the step of moving an element from a first group to a second group in order to correct the grouping of the elements avoids an intermediate step of destruction of the first group or the second group when not empty.

Such a method increases efficiency, and limits the time of processing by the computer.

According to an embodiment, the step of moving an element from a first group to a second group in order to correct the grouping of the elements is performed by a drag and drop technique.

Thus, it is an easy way to perform this step.

According to an embodiment, the step of moving an element from a first group to a second group in order to correct the grouping of the elements comprises a step of creating a temporary empty group.

Thus, it is an easy way to perform the creation of a new group, using the same kind of user interaction.

According to an embodiment, the method comprises the step of activation/de-activation of a group, for example with a check box or tip box.

According to an embodiment, in a group, elements are distinguishable by a respective representation, like a dedicated color, icon, or pattern.

It is proposed, according to another aspect of the invention, a computer-readable medium having computer-executable instructions to cause the computer system to perform the method for designing a biological model as described above.

It is proposed, according to another aspect of the invention, a computer program product, stored on a computer readable medium, for designing a biological model, comprising code means for causing the system to take the steps as described above.

It is proposed, according to another aspect of the invention, an apparatus for designing a biological model comprising means for implementing the steps of the method as described above.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

The invention will be better understood with the study of some embodiments described by way of non-limiting examples and illustrated by the accompanying drawings wherein.

DETAILED DESCRIPTION OF THE INVENTION

A description of example embodiments of the invention follows.

Following figures explain more in details the functioning of the present invention.

After a selection of biological models by the user to compose a combined model, elements from these models are displayed using a partial view. On FIG. 11, each element is represented by its name and, for instance, a pattern in a little rectangle with a specific fill which indicates the origin model of the element.

Figure 1:
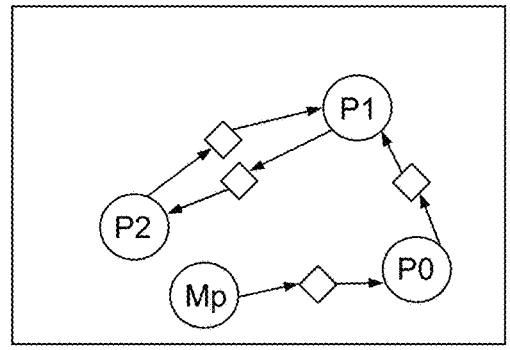
FIGS. 1 to 10 illustrate state of the art for combining or merging biological models.
Figure 2:
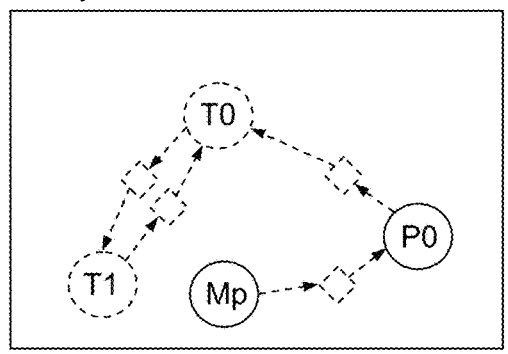
Figure 3:
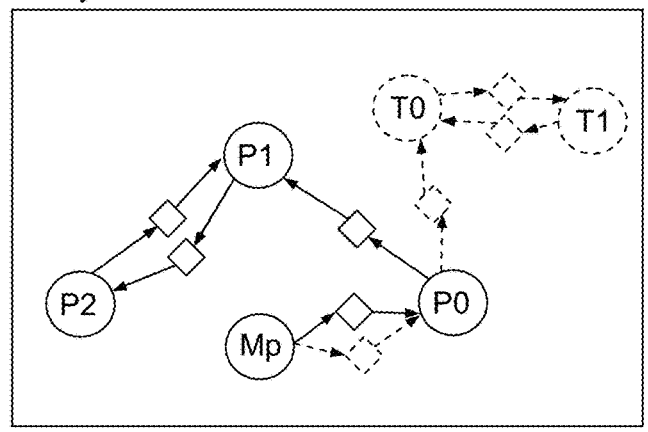
Figure 4:
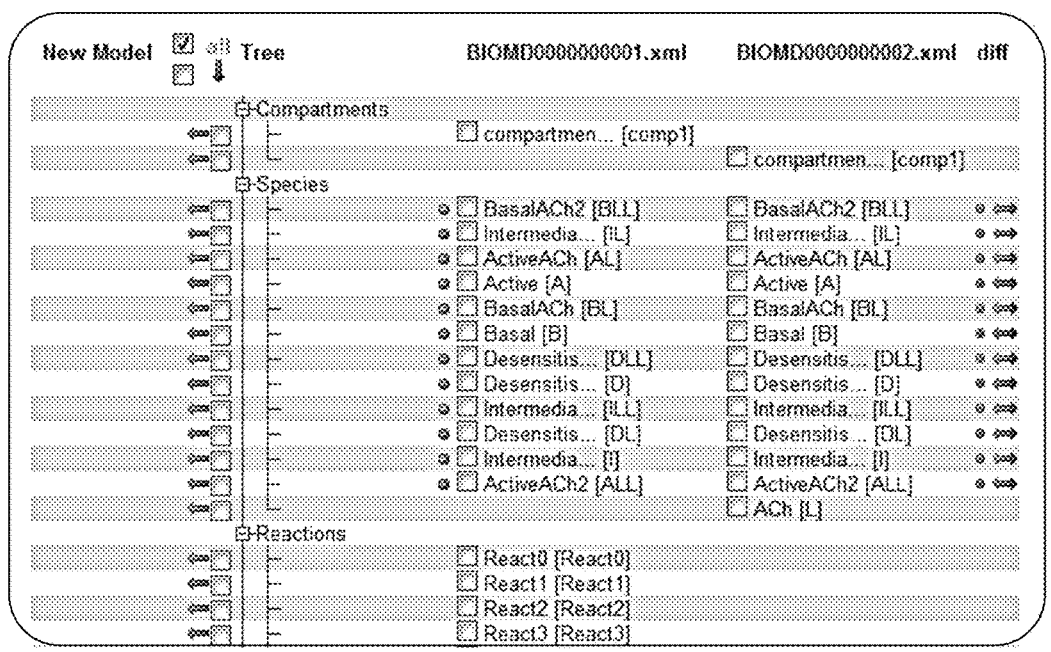
Figure 5:
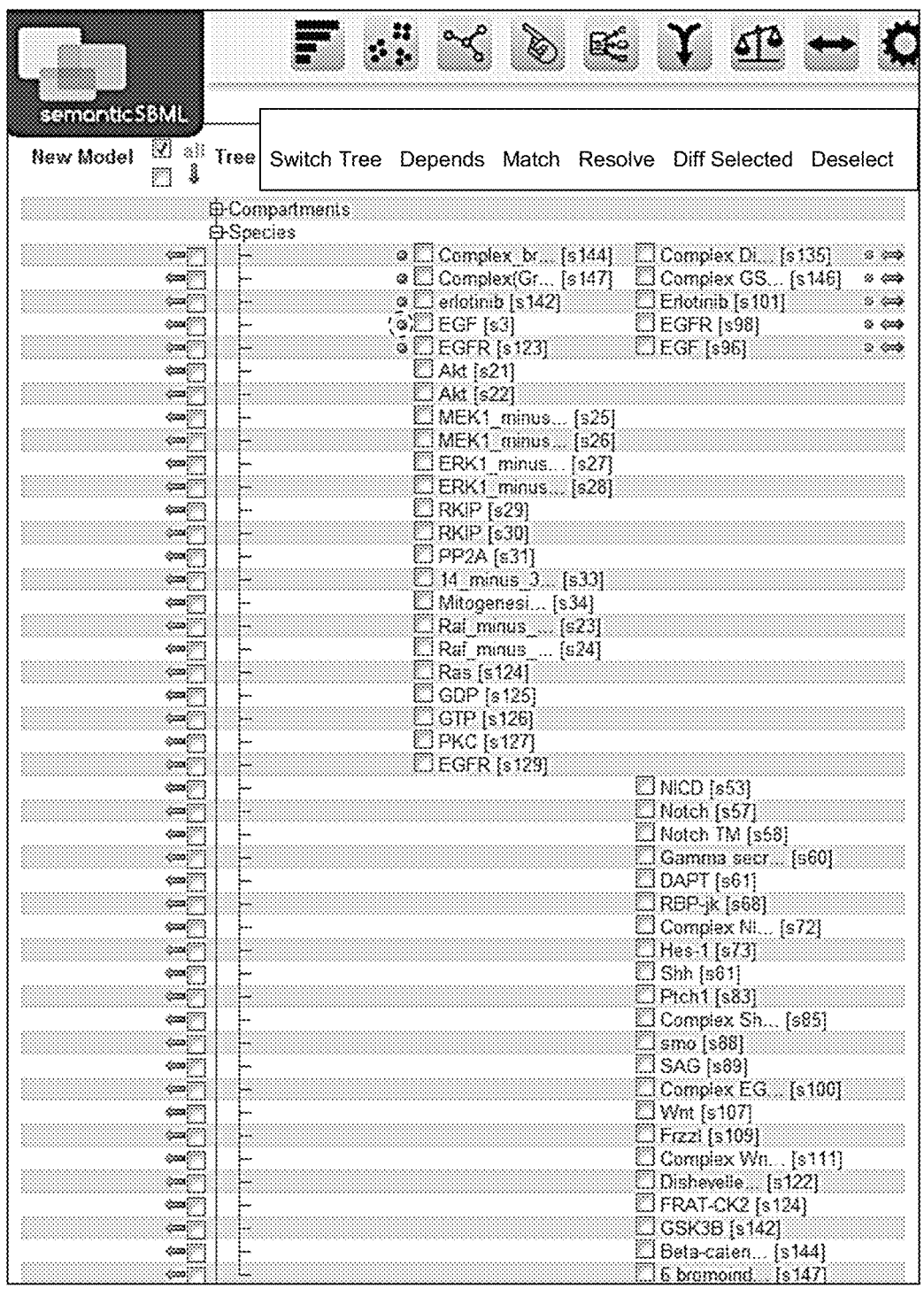
Figure 6:
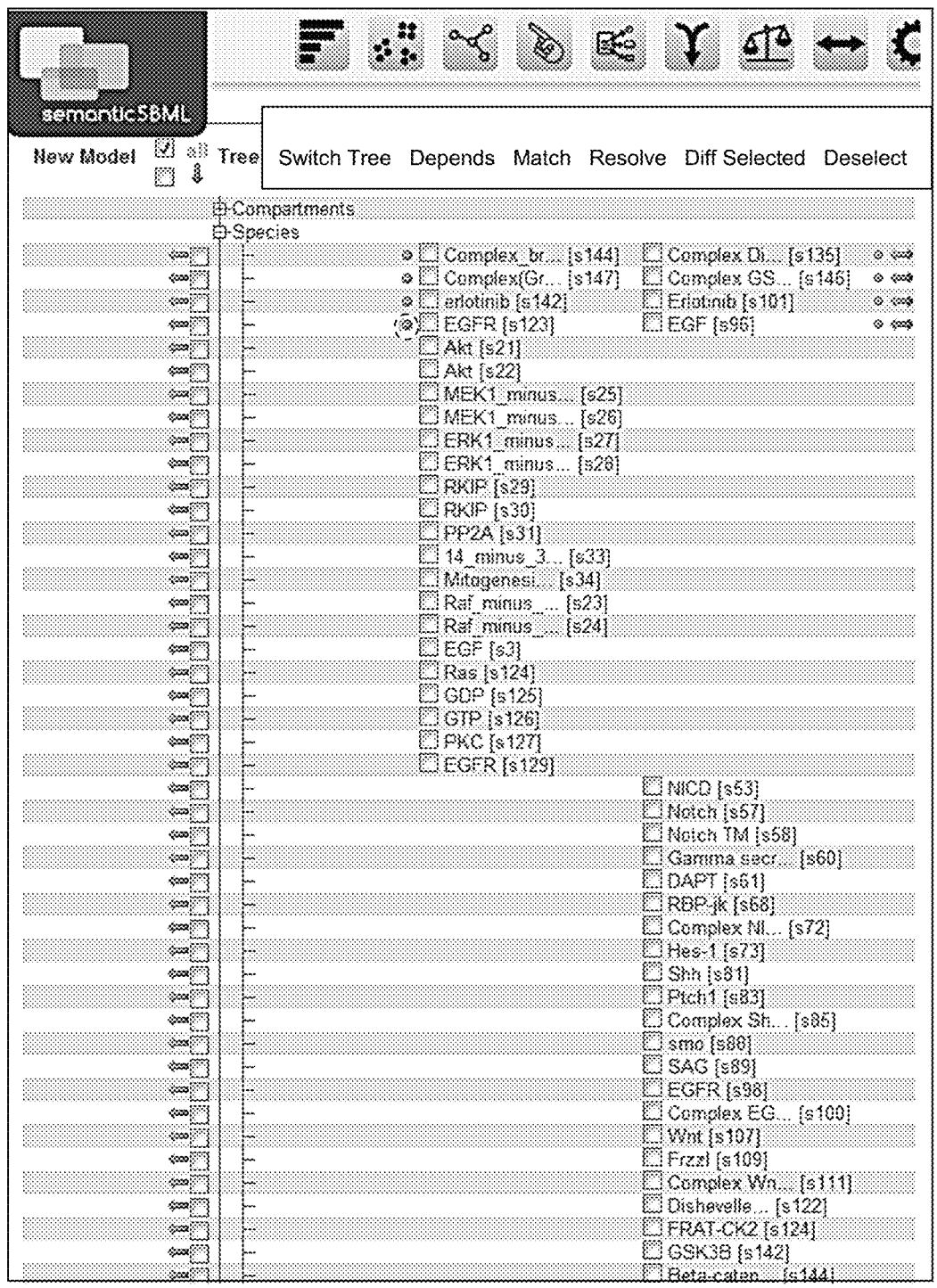
Figure 7:
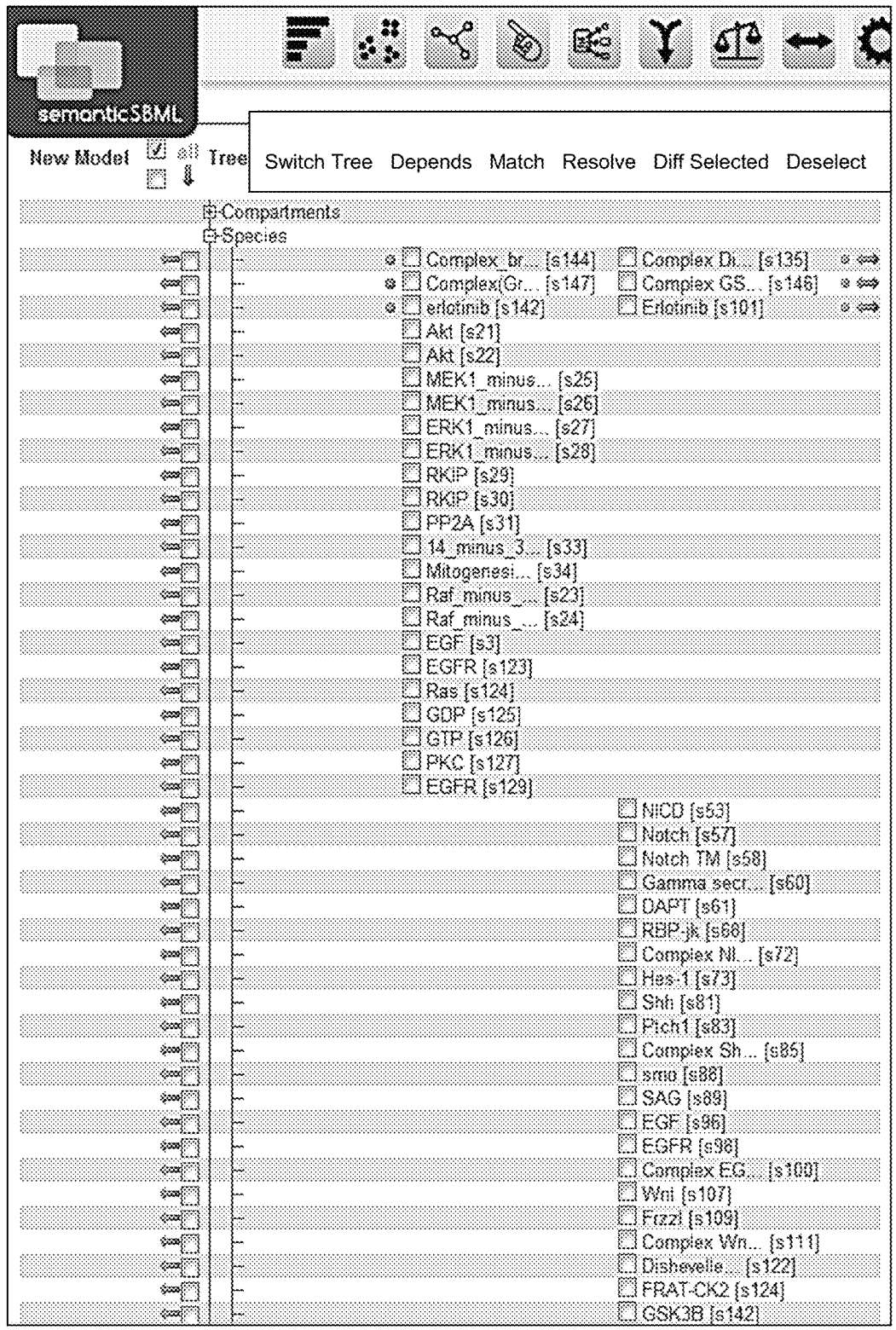
Figure 8:
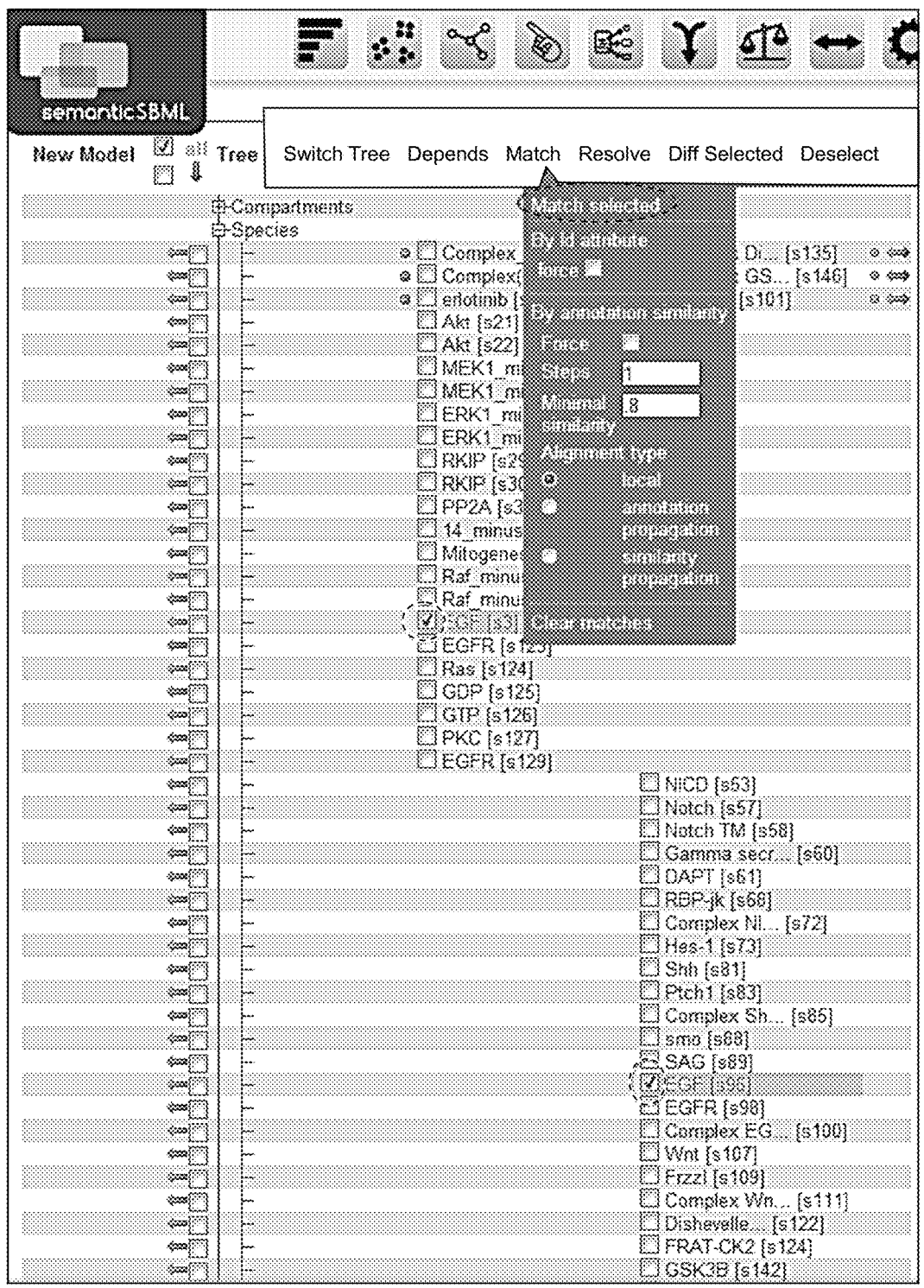
Figure 9:
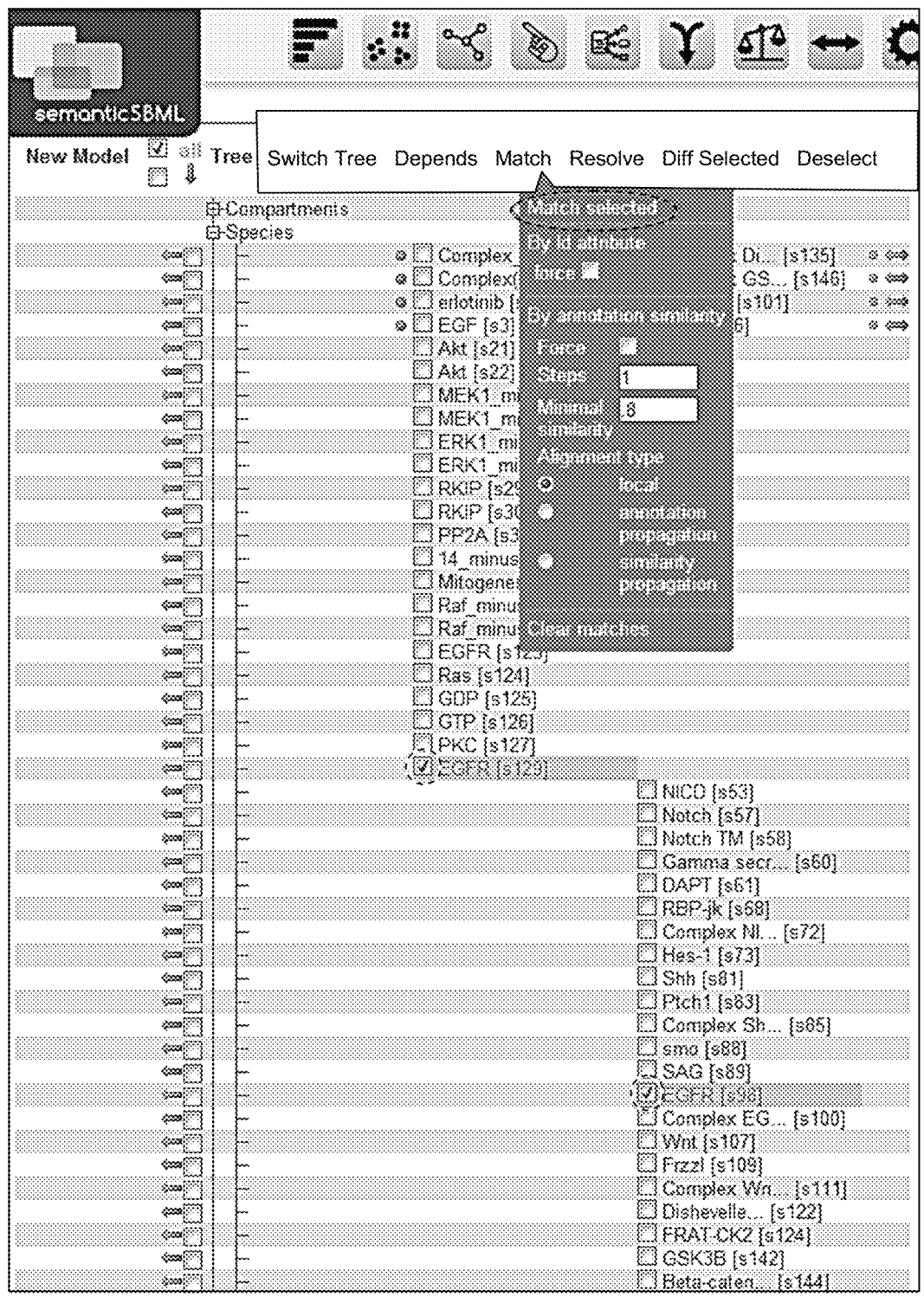
Figure 10:
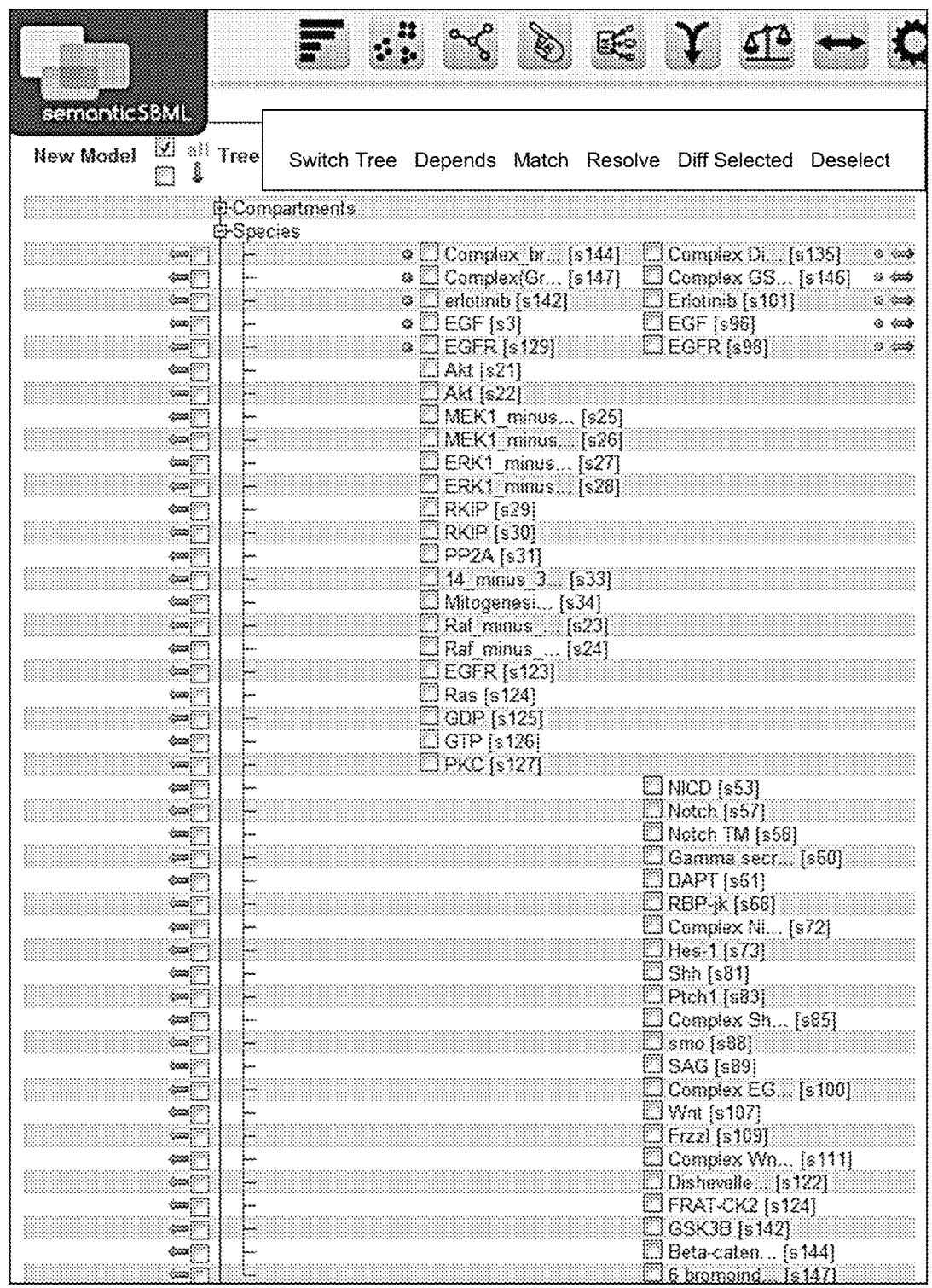
Figure 11:
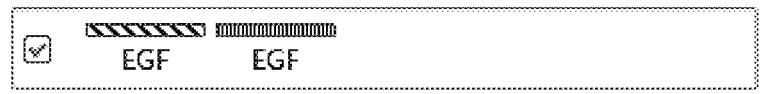
FIGS. 11 to 26 illustrate an example of computer-implemented method for designing a biological model, according to an aspect of the invention.

If different model elements are displayed as grouped, it means that they are likely to be merged together. Such a group is named a "merging group". FIG. 11 represents one merging group.

A merging group also contains a checkbox. The user can check it if he wants to consider the merging proposal or uncheck it if he wants to ignore it.

Figure 12:
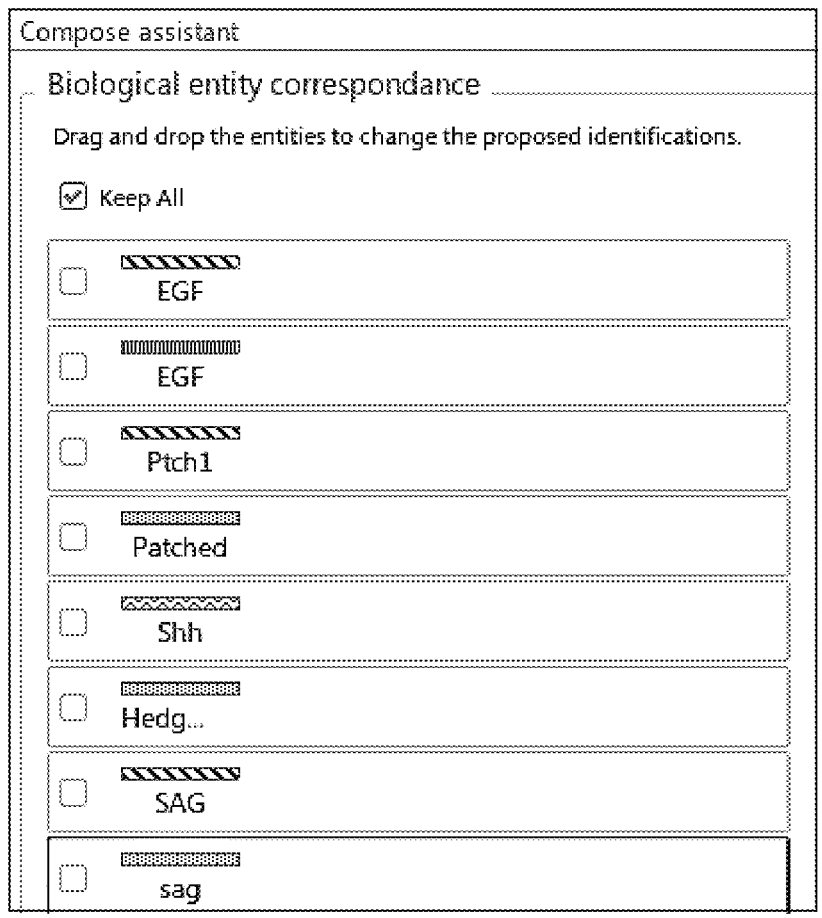
Figure 13:
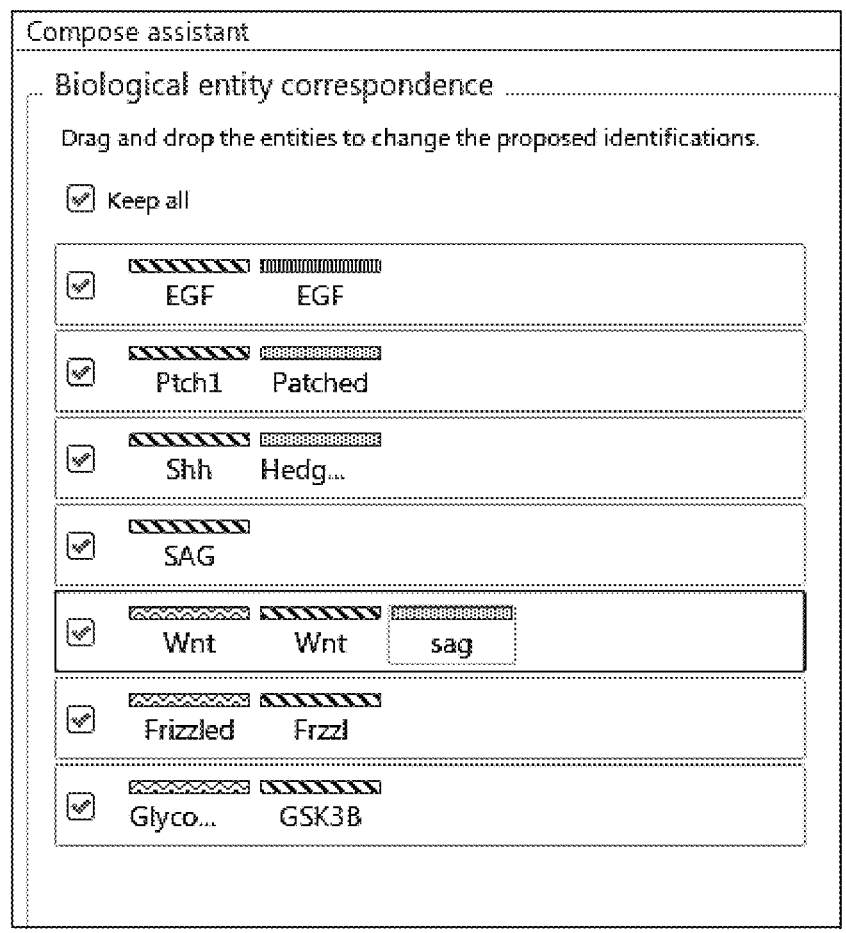

If the merging process is only manual, an initial list with as many merging groups as the total number of elements is displayed to the user, each group containing one model element, as for example illustrated on FIG. 12. If a merging algorithm is provided, the initialization of the list comes from the algorithm result, as for example illustrated on FIG. 13.

Figure 14:
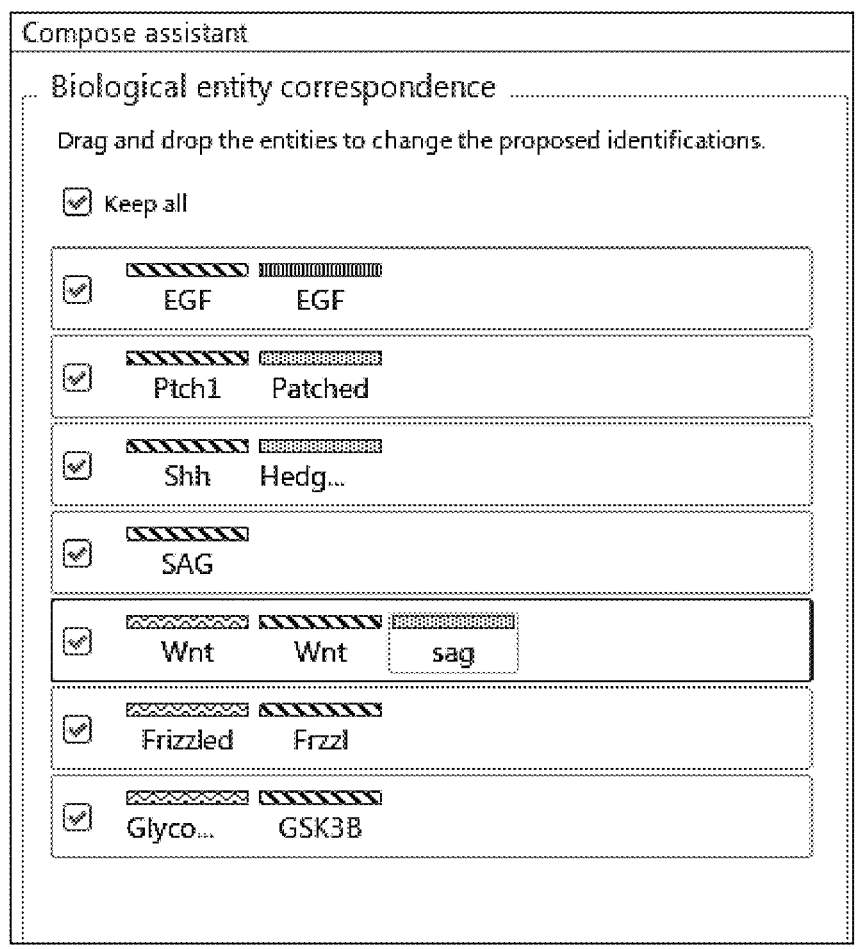
Figure 15:
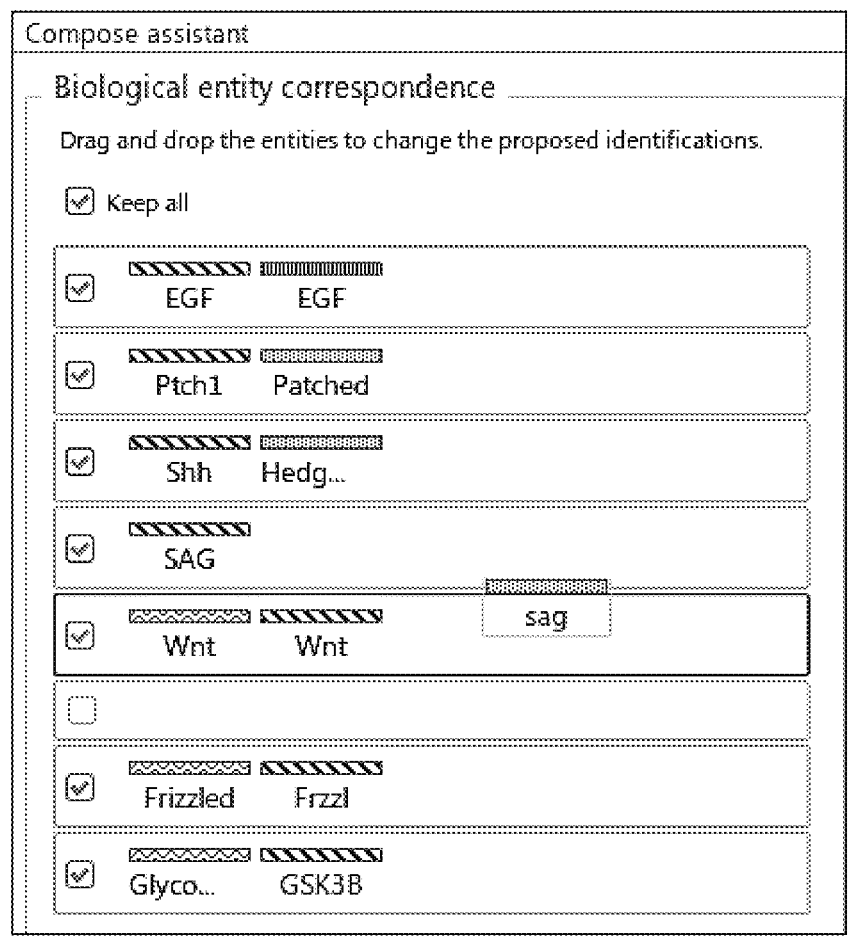
Figure 16:
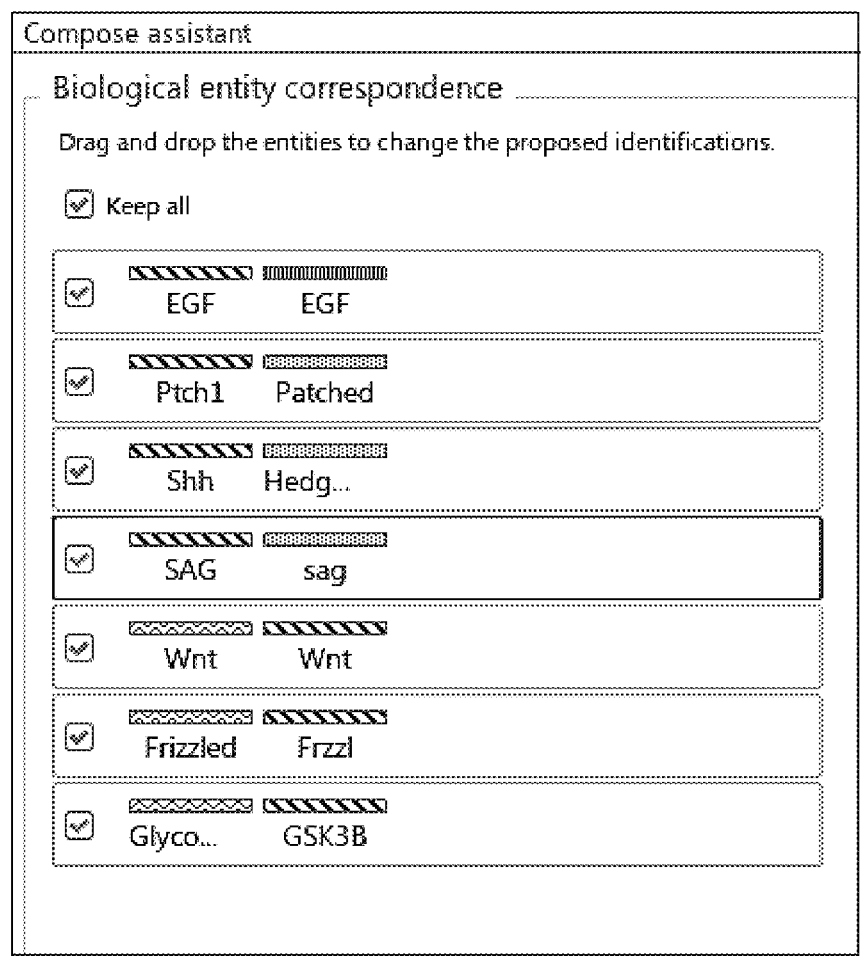

The specific character of the present method concerns the way to modify the merging proposal list. FIGS. 14, 15 and 16 illustrate a random step in the merging process. In the present example, seven merging groups are initially represented.

The user can change the current state of merging groups with a full expressivity using a single atomic interaction. This interaction can be implemented by a drag and drop.

In the example, the user drags the element "sag" element from the fifth merging group and drops it to the fourth one. As a result, element "sag" is then identified with element "SAG" of the fourth merging group.

Figure 17:
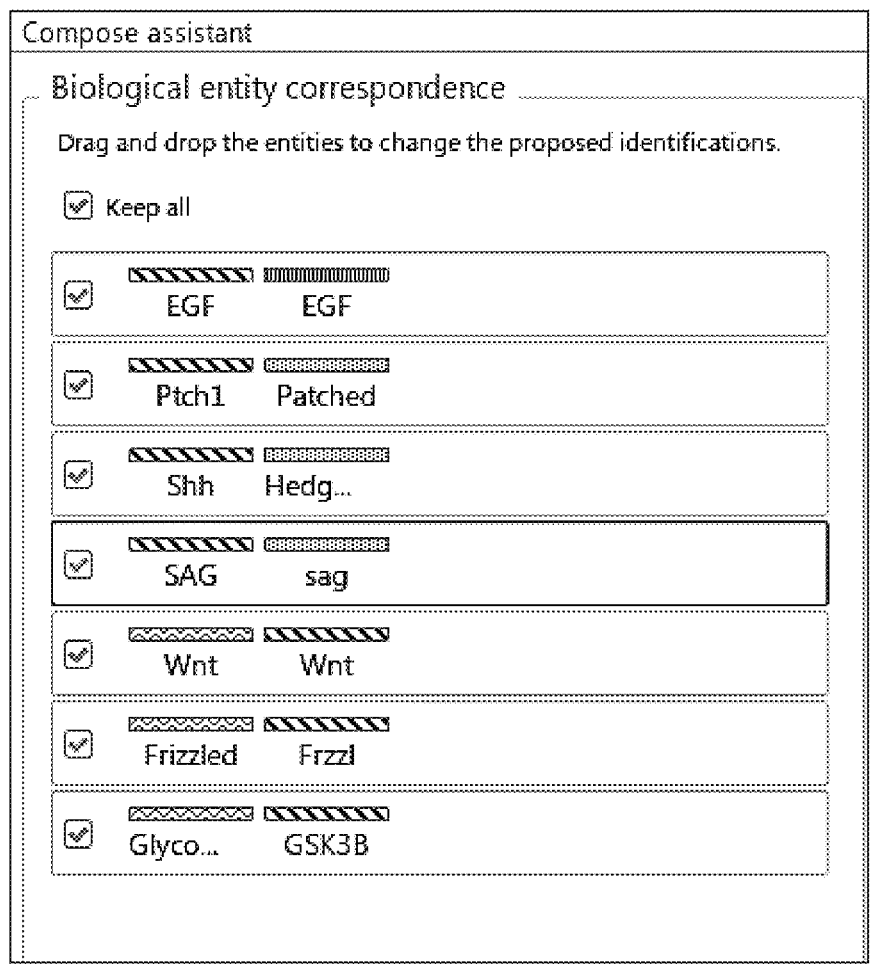
Figure 18:
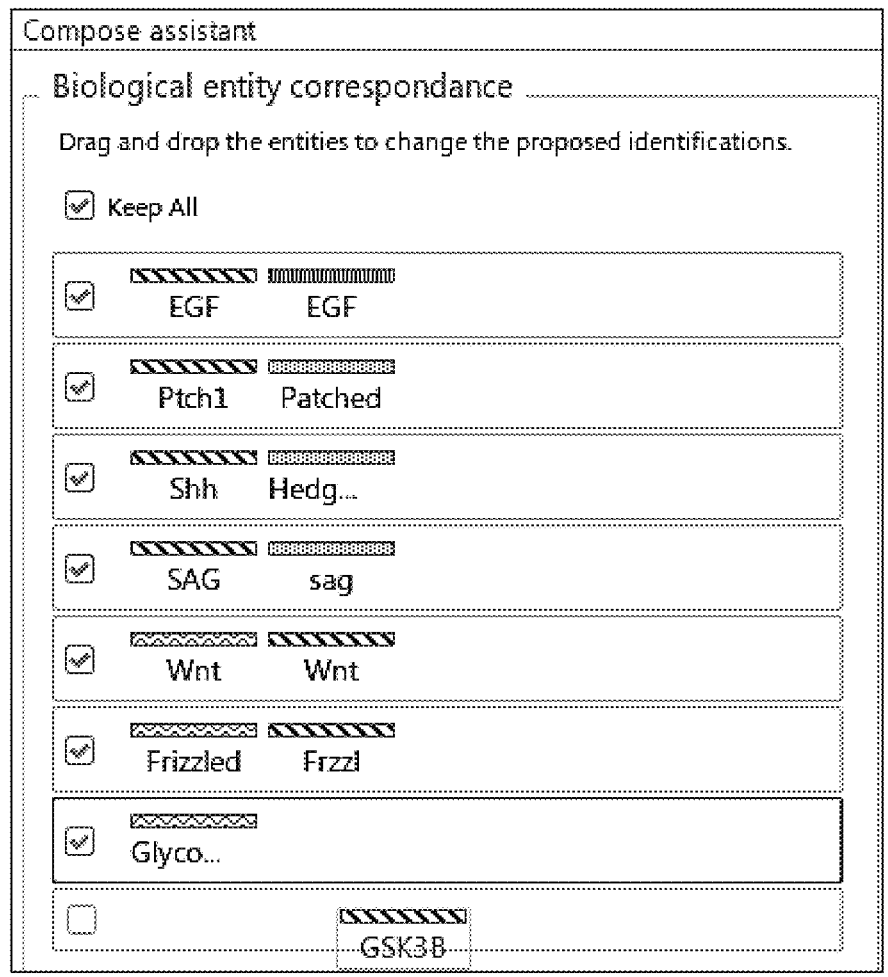
Figure 19:
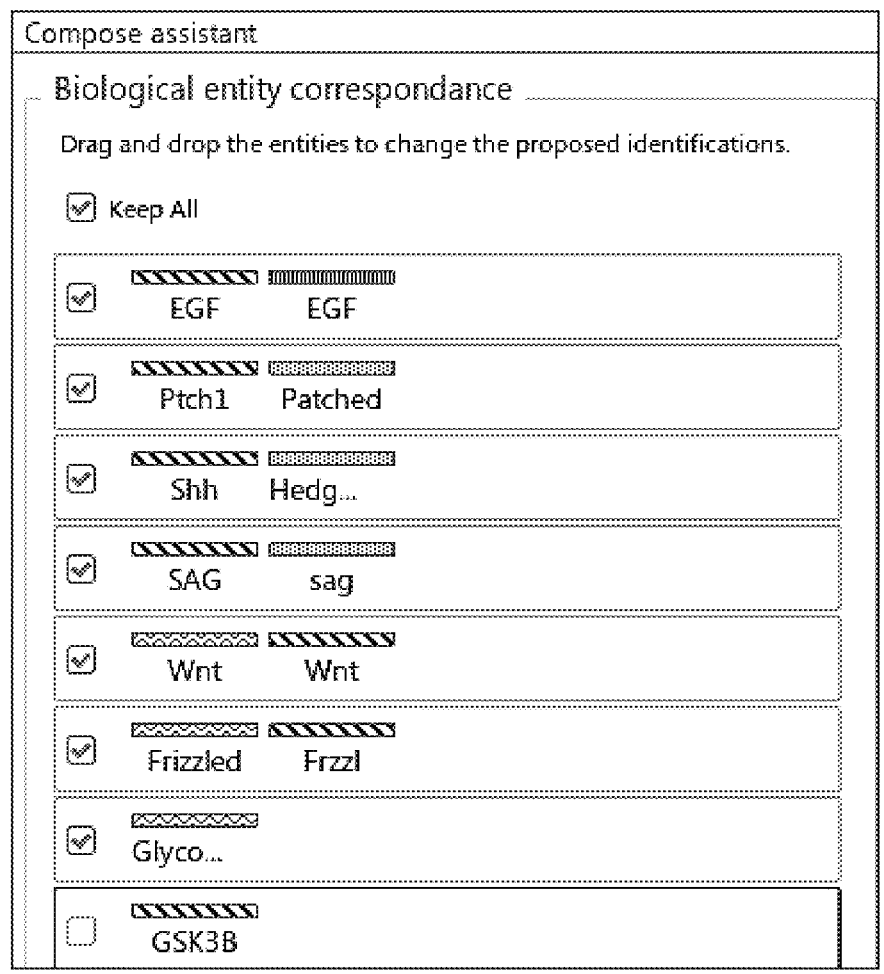

A particular case of the method is the creation of a new merging group. In the example illustrated on FIGS. 17, 18 and 19, the user removes GSK3B from the last merging group.

In order to help the user in the merging process, a contextual view is provided, based on the selected merging group. This contextual view consists of a graph with all the elements (Frizzled) of the merging group represented a single node, completed by the two-level neighborhood (Wnt, Complex Wnt-Frzzl) of the element in each origin model. The same legend as above is used to indicate the origin model of each represented node. A specific legend is used for the "merging group node" (here, a checked pattern).

Figure 20:
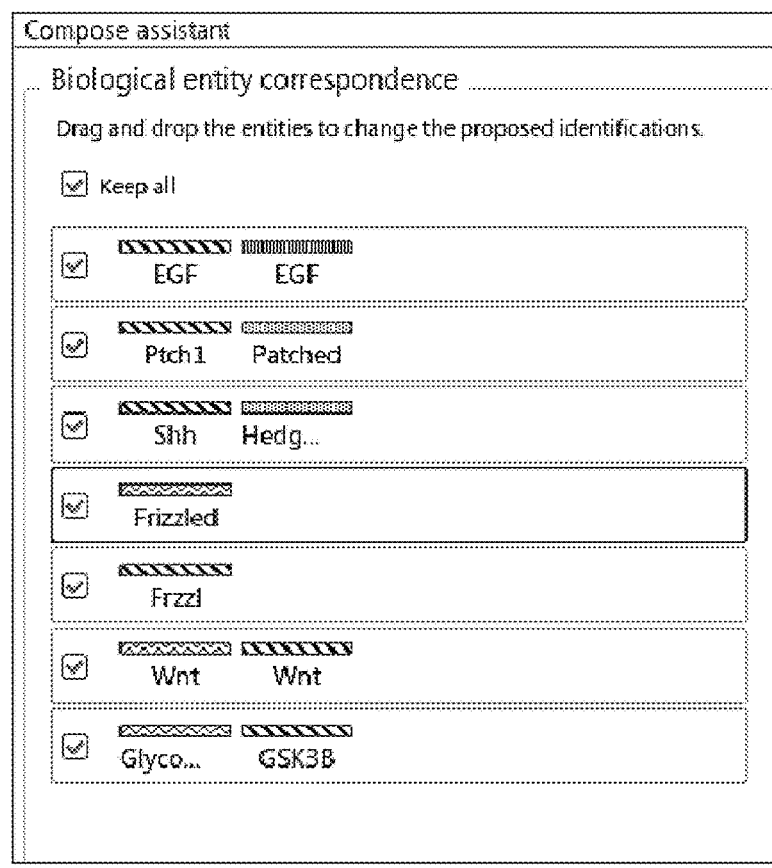
Figure 21:
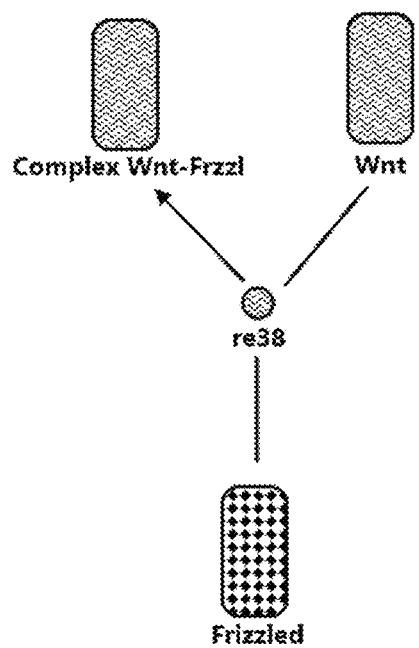

On FIGS. 20 and 21, element Frizzled is selected from the wave model, its neighbors (Wnt, Complex Wnt-Frzzl) are represented on the right. "re38" represents the interaction between Frizzled, Wnt and Complex Wnt-Frzzl: the reaction between a Wnt and a Frizzled gives a "Complex Wnt-Frzzl".

Figure 22:
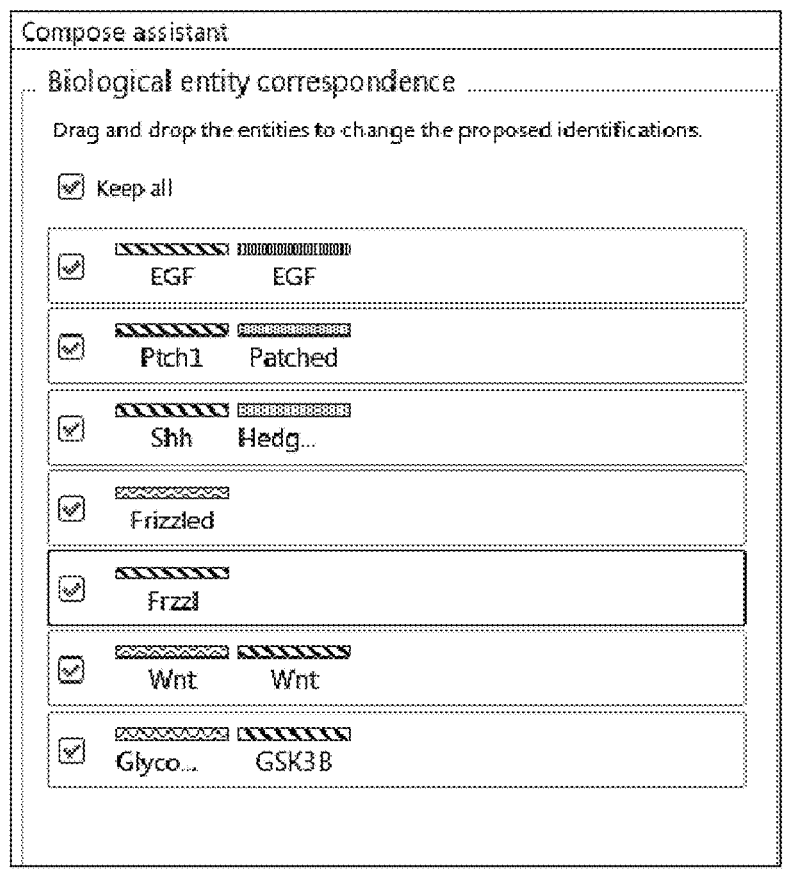
Figure 23:
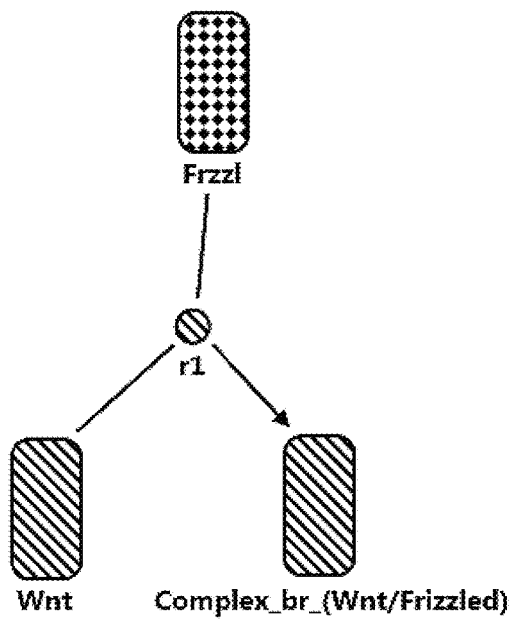

On FIGS. 22 and 23, element Frzzl is selected from the striped model, its neighbors (Wnt, Complex_br_(Wnt/Frizzled) are represented on the right. "r1" represents the interaction between Frzzl, Wnt and the complex.

Figure 24:
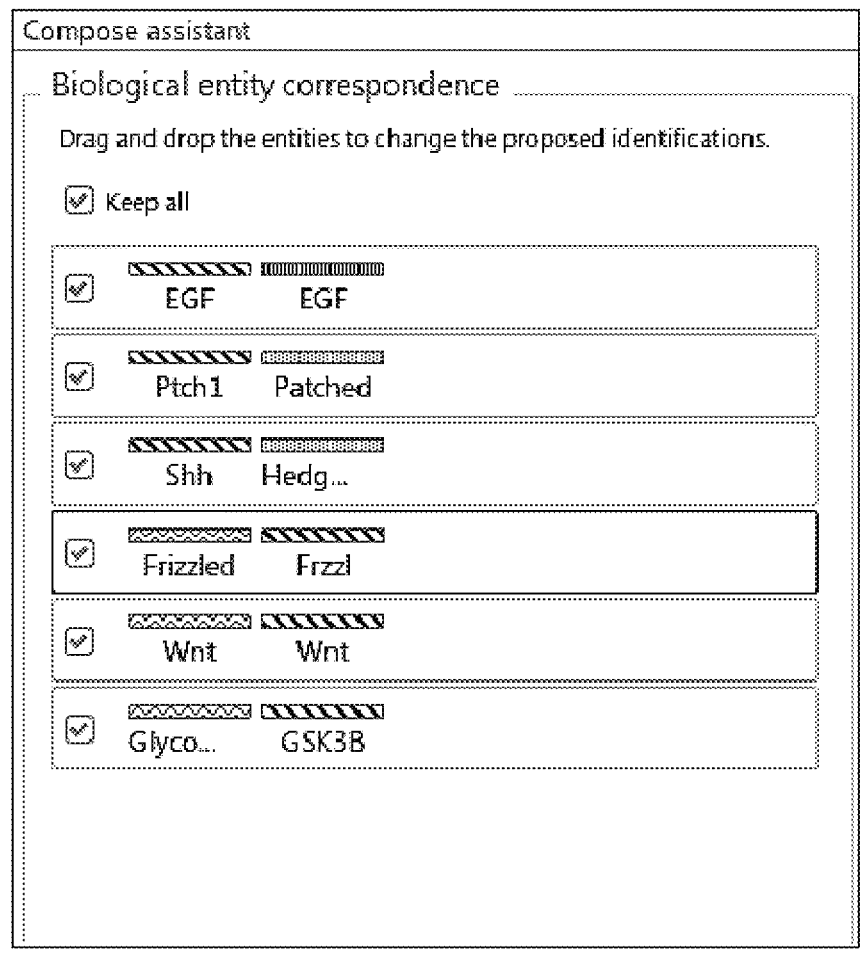
Figure 25:
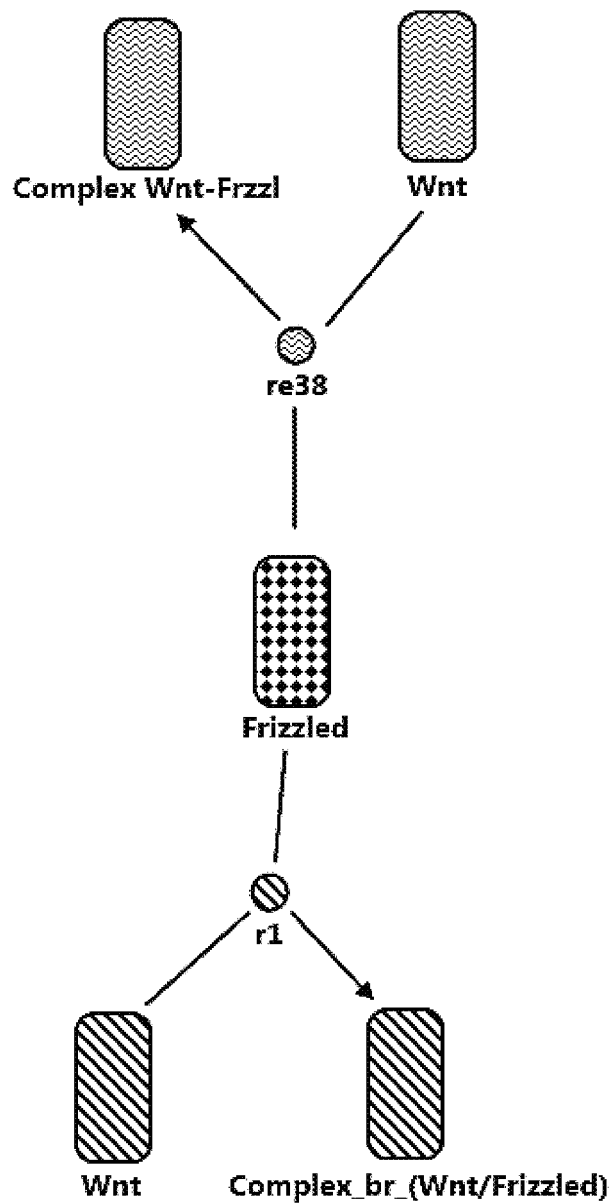

On FIGS. 24 and 25, the "Frizzled-Frzzl" merging group is selected, neighbors of both Frizzled and Frzzl are represented on the right, with a legend to understand from which model they come.

The final combined model ending previous manipulations is not represented on a figure, because, for this example, the size of the combined model is too important for an application patent drawing.

Figure 26:
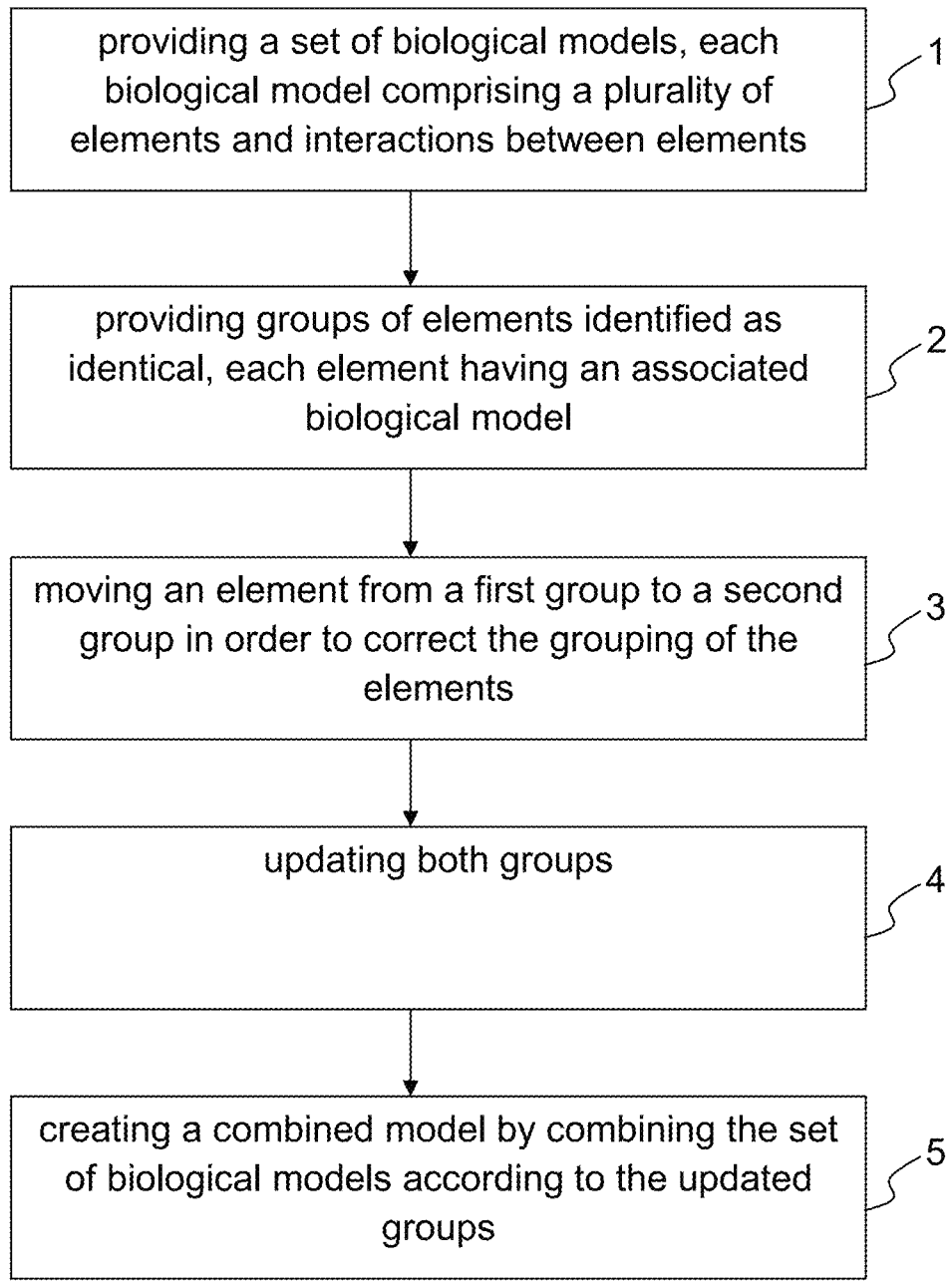

FIG. 26 illustrates the steps of the computer-implemented method according to an aspect of the invention for designing a biological model comprising the steps of:
providing (1) a set of biological models, each biological model comprising a plurality of elements and interactions between elements;
providing (2) groups of elements identified as identical, each element having an associated biological model;
moving (3) an element from a first group to a second group in order to correct the grouping of the elements;
updating (4) both groups; and
creating (5) a combined model by combining the set of biological models according to the updated groups.

Figure 27:
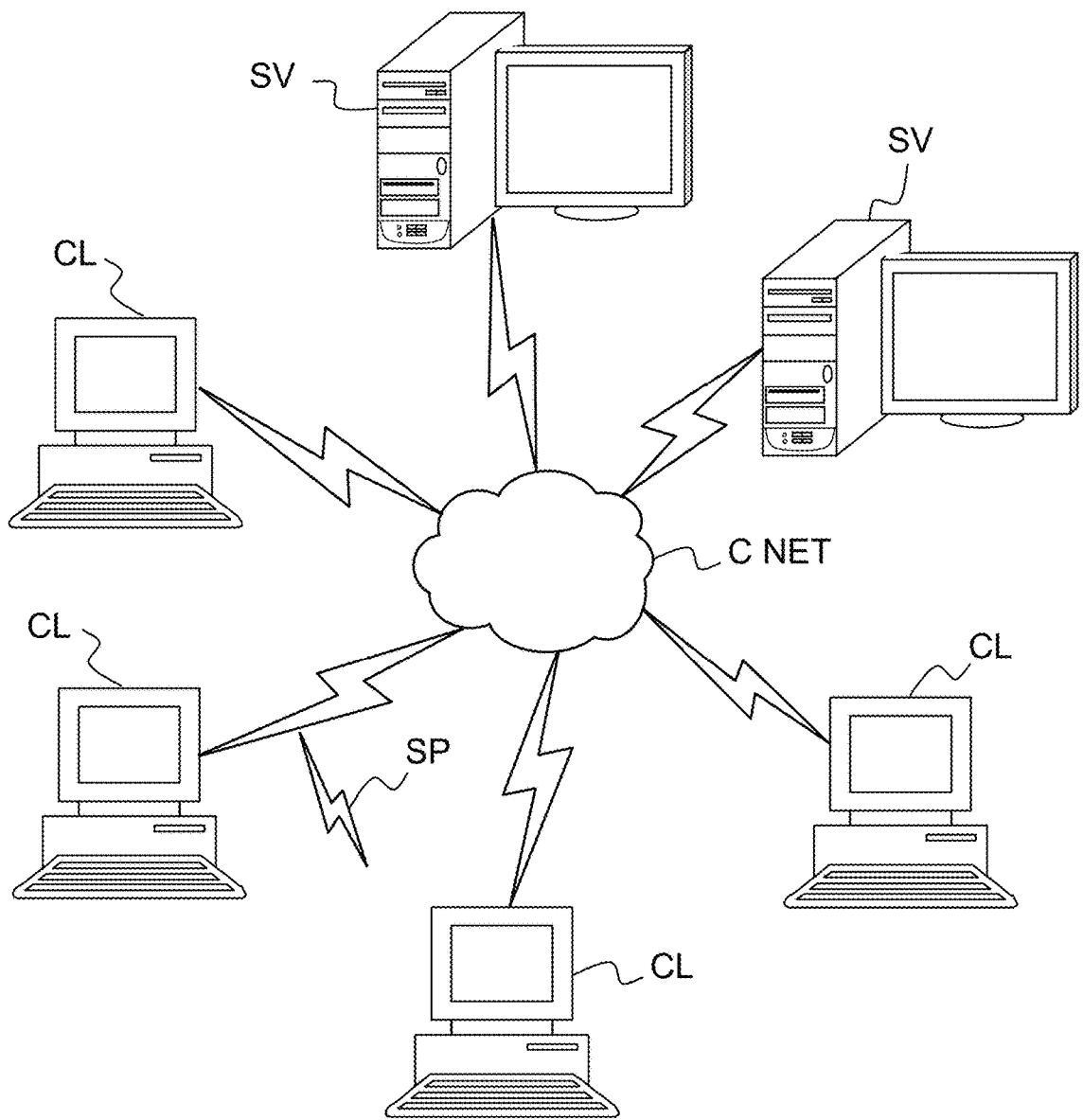
FIG. 27 illustrates a computer network or similar digital processing environment in which the present invention may be implemented.

FIG. 27 illustrates a computer network or similar digital processing environment in which the present invention may be implemented.

Client computer(s)/devices CL and server computer(s) SV provide processing, storage, and input/output devices executing application programs and the like. Client computer(s)/devices CL can also be linked through communications network CNET to other computing devices, including other client devices/processes CL and server computer(s) SV. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 28:
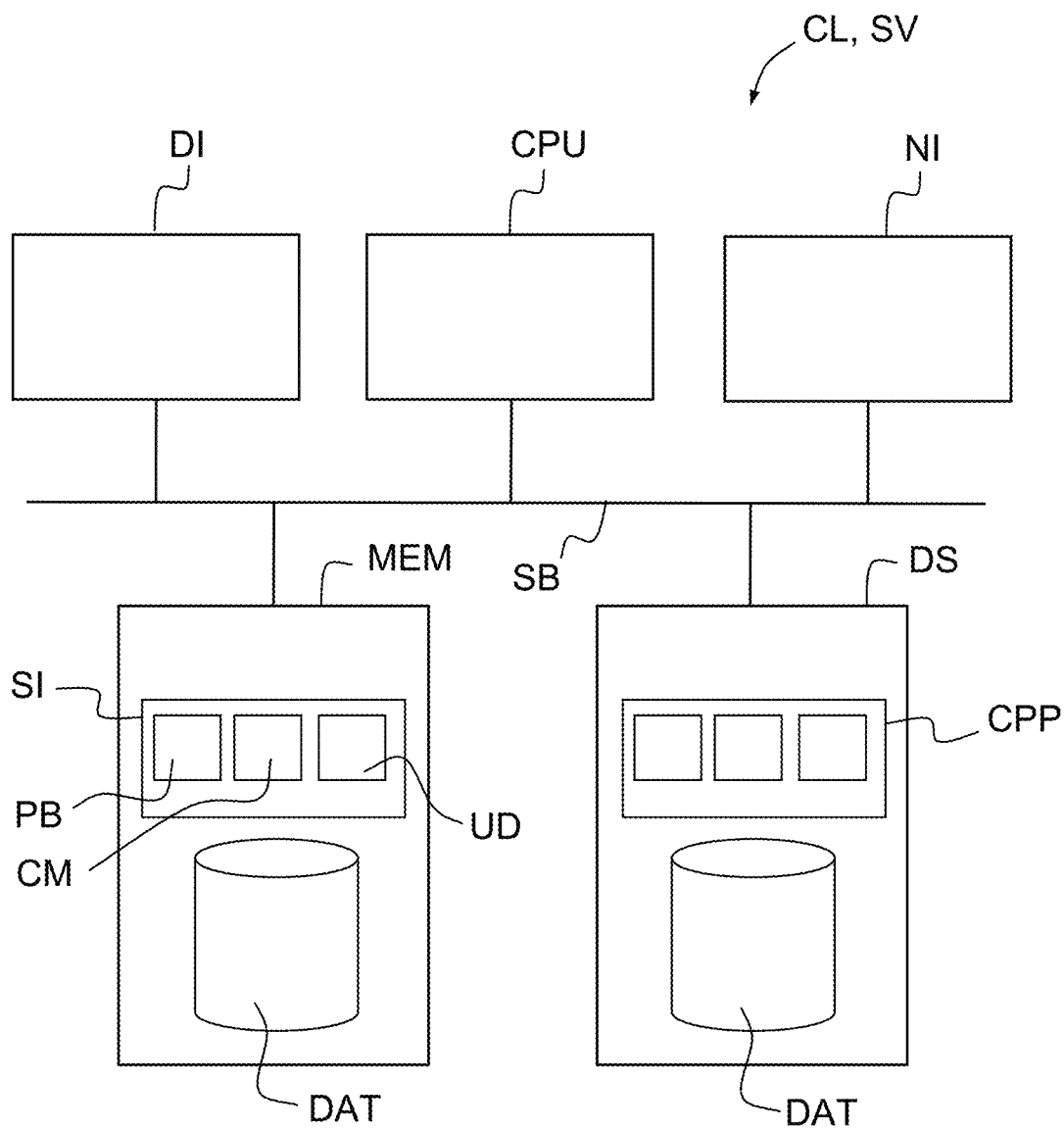
FIG. 28 illustrates a diagram of the internal structure of a computer.

FIG. 28 is a diagram of the internal structure of a computer (e.g., client processor/device CL or server computers SV) in the computer system of FIG. 26. Each computer CL, SV contains system bus SB, where a bus is a set of hardware lines used for data transfer among the components of a computer or processing system. Bus SB is essentially a shared conduit that connects different elements of a computer system (e.g., processor, disk storage, memory, input/output ports, network ports, etc . . . ) that enables the transfer of information between the elements.

Attached to system bus SB is I/O device interface DI for connecting various input and output devices (e.g., keyboard, mouse, displays, printers, speakers, etc.) to the computer CL, SV. Network interface NI allows the computer to connect to various other devices attached to a network (e.g., network CNET of FIG. 27).

Memory MEM provides volatile storage for computer software instructions SI and data CPP used to implement an embodiment of the present invention (e.g., a first path builder PB, means CM for computing a second path, an updater UD implementing the method discussed in FIGS. 1 to 26, and supporting code detailed above).

Disk storage DS provides non-volatile storage for computer software instructions SI and data DAT used to implement an embodiment of the present invention. Central processor unit CPU is also attached to system bus SB and provides for the execution of computer instructions.

In one embodiment, the processor routines SI and data DAT are a computer program product (generally referenced CPP), including a computer readable medium (e.g., a removable storage medium such as one or more DVD-ROM's, CD-ROM's, diskettes, tapes, etc . . . ) that provides at least a portion of the software instructions for the invention system. Computer program product CPP can be installed by any suitable software installation procedure, as is well known in the art.

In another embodiment, at least a portion of the software instructions may also be downloaded over a cable, communication and/or wireless connection. In other embodiments, the invention programs are a computer program propagated signal product SP embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program CPP.

In alternate embodiments, the propagated signal is an analog carrier wave or digital signal carried on the propagated medium. For example, the propagated signal may be a digitized signal propagated over a global network (e.g., the Internet), a telecommunications network, or other network.

In one embodiment, the propagated signal is a signal that is transmitted over the propagation medium over a period of time, such as the instructions for a software application sent in packets over a network over a period of milliseconds, seconds, minutes, or longer.

In another embodiment, the computer readable medium of computer program product CPP is a propagation medium that the computer system CL may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

While this invention has been particularly shown and described with references to example embodiments thereof, it will be understood by those skilled in the art that various changes in form and details may be made therein without departing from the scope of the invention encompassed by the appended claims.

The teachings of all patents, published applications and references cited herein are incorporated by reference in their entirety.

What is claimed is:

1. A computer-implemented method for designing a biological model, the method comprising:
displaying a user-interface having groups of elements identified as identical, each element having an associated biological model of a set of biological models, each biological model comprising a plurality of elements and interactions between elements, the plurality of elements being biological molecules;

enabling a drag and drop user input within the user-interface that selects a particular element from a first group of the group of elements, drags the particular element from the first group of the group of elements to a second group of the group of elements, and releases the particular element near the second group;

responsive to receiving the drag and drop user input, updating the first group to remove the particular element and the second group to include the particular element; and creating a combined model by combining the set of biological models according to the updated groups.

2. The computer-implemented method of claim 1, wherein displaying groups of elements identified as identical uses annotations attached to the biological models (A, B).

3. The computer-implemented method of claim 1, wherein displaying a set of biological models (A, B) loads the set of biological models from at least one external database.

4. The computer-implemented method of claim 1, further comprising:

partially representing the biological models around a common element, with a common annotation, in case of acceptance of the corresponding merging suggestion.

5. The computer-implemented method of claim 1, wherein enabling user input to move an element from a first group to a second group avoids an intermediate step of destruction of the first group or the second group when not empty.

6. The computer-implemented method of claim 1, wherein enabling user input to move an element from a first group to a second group further comprises creating a temporary empty group.

7. The computer-implemented method of claim 1, further comprising activating/de-activating of a group.

8. The computer-implemented method of claim 1, wherein, in a group, elements are distinguishable by a respective representation.

9. A computer program product comprising:

a non-transitory computer readable medium, for designing a biological model; and computer-executable instructions embodied on the computer readable medium including computer-executable instructions that cause a computer system to:

displaying a user-interface having groups of elements identified as identical, each element having an associated biological model of a set of biological models, each biological model comprising a plurality of elements and interactions between elements, the plurality of elements being biological molecules;

enabling a drag and drop user input within the user-interface that selects a particular element from a first group of the group of elements, drags the particular element from the first group of the group of elements to a second group of the group of elements, and releases the particular element near the second group;

responsive to receiving the drag and drop user input, update the first group to remove the particular element and the second group to include the particular element; and create a combined model by combining the set of biological models according to the updated groups.

10. An apparatus for designing a biological model comprising:

a processor; and a non-transitory memory operatively coupled to the processor causing the processor to design a biological model by:

displaying a user-interface having groups of elements identified as identical, each element having an associated biological model of a set of biological models, each biological model comprising a plurality of elements and interactions between elements, the plurality of elements being biological molecules;

enabling a drag and drop user input within the user-interface that selects a particular element from a first group of the group of elements, drags the particular element from the first group of the group of elements to a second group of the group of elements, and releases the particular element near the second group;

responsive to receiving the drag and drop user input, updating the first group to remove the particular element and the second group to include the particular element; and creating a combined model by combining the set of biological models according to the updated groups.

11. An apparatus as claimed in claim 10 wherein the processor displaying groups of elements identified as identical uses annotations attached to the biological models (A, B).

12. An apparatus as claimed in claim 10 wherein the processor displaying a set of biological models (A, B) loads the set of biological models from at least one external database.

13. An apparatus as claimed in claim 10 wherein the processor partially represents the biological models around a common element, with a common annotation, in case of acceptance of the corresponding merging suggestion.

14. An apparatus as claimed in claim 10 wherein the processor enabling user input to move an element from a first group to a second group avoids an intermediate step of destruction of the first group or the second group when not empty.

15. An apparatus as claimed in claim 10 wherein the processor enabling user input to move an element from a first group to a second group creates a temporary empty group.

16. An apparatus as claimed in claim 10 wherein the processor further performs activation/de-activation of a group.

17. An apparatus as claimed in claim 10 wherein in a group, elements are distinguishable by a respective representation.

\* \* \* \* \*